United States Patent
Hussein et al.

(10) Patent No.: US 6,264,984 B1
(45) Date of Patent: Jul. 24, 2001

(54) EFFERVESCENT HISTAMINE $H_2$ ANTAGONIST COMPOSITION

(75) Inventors: Mamoun M. Hussein, Mountain Lakes; John Migton, Clark, both of NJ (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/455,233

(22) Filed: Dec. 6, 1999

(51) Int. Cl.$^7$ ...................................................... A61K 9/46
(52) U.S. Cl. ........................... 424/466; 424/464; 424/465; 424/489
(58) Field of Search ...................... 424/466, 465, 424/489

(56) References Cited

U.S. PATENT DOCUMENTS

| | | | |
|---|---|---|---|
| 4,824,664 | 4/1989 | Tarral et al. | 424/43 |
| 5,102,665 | 4/1992 | Schaeffer | 424/466 |
| 5,424,075 | 6/1995 | Daher et al. | 424/465 |
| 5,503,846 * | 4/1996 | Wehling et al. | 424/466 |
| 5,759,575 | 6/1998 | Gergely et al. | 424/466 |
| 5,762,951 | 6/1998 | Maasz | 424/439 |
| 5,792,473 | 8/1998 | Gergely et al. | 424/466 |

FOREIGN PATENT DOCUMENTS

| | | | |
|---|---|---|---|
| 0 233 853 B1 | 9/1990 | (EP) | A61K/9/46 |
| 0 670 160 A1 | 9/1995 | (EP) | A61K/9/46 |
| 0 761 212 A2 | 9/1996 | (EP) | A61K/9/46 |
| 0 761 212 A3 | 9/1996 | (EP) | A61K/9/46 |
| 95/10274 | 10/1993 | (WO) | A61K/31/34 |

* cited by examiner

*Primary Examiner*—Thurman K. Page
*Assistant Examiner*—Liliana Di Nola-Baron
(74) *Attorney, Agent, or Firm*—Charles J. Zeller; Theodore R. Furman, Jr.

(57) ABSTRACT

A histamine $H_2$ antagonist incompatible with acidic materials is incorporated in an effervescent composition and is stable therein provided the acidulant employed in the effervescent couple is a non-hydroxy group containing acidulant and such acidulant is employed as substantially the entire amount of the acidulant present in the formulation. Preferably the composition is devoid of hydroxy group containing acidulant. Adipic acid, succinic acid, fumaric acid and succinic anhyride may be employed as the acidulant. Adipic acid is preferred.

15 Claims, No Drawings

EFFERVESCENT HISTAMINE $H_2$ ANTAGONIST COMPOSITION

FIELD OF THE INVENTION

This invention relates to effervescent compositions containing histamine $H_2$ antagonists incompatible with acidulants and more particularly, it relates to effervescent histamine H2 antagonists containing compositions containing certain acidulants found to be compatible with such antagonists.

BACKGROUND OF THE INVENTION

Effervescent compositions usually comprise excipients, active ingredients, and a source of carbon dioxide typically referred to as an effeverscent couple. Effervescent couples are usually composed of an alkaline bicarbonate or carbonate and an acid. In the presence of water, the alkaline bicarbonate or carbonate and the acid generate carbon dioxide. Thus, effeverscent compositions are extremely sensitive to moisture. This necessitates special steps to protect the raw materials and the finished formulation from exposure to moisture, throughout the manufacturing process and thereafter. Anhydrous citric acid is the most commonly employed acidulant in the manufacture of effeverscent compositions. Anhydrous citric acid is however, extremely hygroscopic. So also are the most commonly employed sources of carbon dioxide, i.e, alkali bicarbonates and carbonates.

The aforementioned problems are compounded when an effervescent composition is to contain, as the active, a histamine $H_2$ antagonist. Histamine $H_2$ antagonists are incompatible with acids, particularly the acids employed in effervescent compositions. Published EP Patent specification No. 233853 discloses that use of citric acid in effervescent compositions containing a histamine $H_2$ antagonist evidences incompatibility of the $H_2$ antagonist with the acids contained in the effervescent composition. In an effort to resolve this, citric acid was replaced by a mixture of mono- and di- alkaline citrates.

U.S. Pat. No. 4,824,664 teaches that histamine $H_2$ antagonists are not stable with the acids contained in effervescent products. They endeavor to overcome this instability by granulating the effervescent mixture and generating during such granulation a mixture of mono- and di- alkali citrate in a specified ratio.

U.S. Pat. No. 5,102,665 teaches preparation of a stable effervescent ranitidine using mono-alkali citrate as the sole acidulant. The effervescent system disclosed therein is granulated in alcohol prior to manufacturing the composition.

SUMMARY OF THE INVENTION

In light of the above teaching of the prior art, one skilled in the art would, in view of the known incompatibility of histamine $H_2$ antagonists, and in particular, ranitidine, with acids employed in effervescent products would refrain from making such a combination. Surprisingly and unexpectedly, the present inventors have discovered that certain acids (i.e., non-hydroxy group containing acidulants) can be incorporated in effervescent compositions containing histamine $H_2$ antagonists and that the resultant compositions are stable. In other words, surprisingly and unexpectedly, the histamine $H_2$ antagonists are stable in effervescent compositions of the present invention.

DETAILED DESCRIPTION OF THE INVENTION

The acidulants that can be utilized in preparing the effervescent histamine $H_2$ antagonist compositions of the present invention are non-hydroxy group containing acidulants. For example, adipic acid, succinic acid, fumaric acid or a derivative thereof that hydrolyzes to form a non-hydroxy group containing acidulants, for example, succinic anhydride.

Although small amounts of a hydroxy containing acidulant may be incorporated in the effervescent composition of the present invention, the composition of the present invention most desirably employs as substantially all of the acidulant, a non-hydroxy group containing acidulant. Most preferably the composition of the present invention is devoid of hydroxy group containing acidulant. In some instances a very small amount of hydroxy group containing acidulant can be tolerated in the composition.

As noted earlier, the present inventors discovered that citric acid, a hydroxy group containing acidulant typically employed in effervescent compositions is incompatible with histamine $H_2$ antagonists when they are incorporated in effervescent compositions. Moreover, malic acid and other hydroxy group containing acidulants present even more of a problem than citric acid. Tartaric acid also presents a compatibility problem, but less than citric acid.

Surprisingly and unexpectedly, the present inventors discovered that when the hydroxy group containing acidulant (such as citric acid and tartaric acid) employed in a histamine $H_2$ antagonist containing effervescent formulation, as part of the effervescent couple, is replaced by a non-hydroxy group containing acidulant (such as adipic acid or succinic acid), in an amount equivalent to the hydroxy group containing acidulant, the resultant effervescent product has acceptable taste, stability and effervescence. Thus, the present invention enables the preparation of histamine $H_2$ antagonist containing effervescent products, by simple dry mixing of ingredients without the need for alkaline metal mono- or di- citrates, (whether added as such, or generated in the effervescent system by wet granulation) and without the need for an effervescent couple containing citric acid.

The compositions of the present invention contain, as an active, a histamine $H_2$ antagonist. The histamine $H_2$ antagonist is preferably selected from the group consisting of ranitidine, cimetidine, famotidine and nizatidine, and pharmaceutically acceptable salts thereof. Ranitidine and cimetidine are more preferred. Ranitidine and its pharmaceutically acceptable salts are most preferred.

The amount of ranitidine, in the form of its salt, may be from 40 to 300 mg, preferably in the range of 50 to 150 mg and most preferably from 50 to 75 mg per dosage unit.

The histamine $H_2$ antagonist is generally present in the composition in an amount such that a dose of the composition will contain such amount of the histamine $H_2$ antagonist as has been approved by the applicable governmental health authority for prescriptive ("$R_x$") or over-the-counter ("O.T.C.") use. In the United States such amounts are as follows:

|  | OTC Dose | $R_x$ Dose |
| --- | --- | --- |
| Ranitidine | 75 mg | 150–300 mg |
| Cimetidine | 200 mg | 300–800 mg |
| Famotidine | 10 mg | 20–40 mg |
| Nizatidine | 75 mg | 150–300 mg |

The effervescent couple employed in the compositions of the present invention is comprised of an alkaline component and an acidulant. The alkaline component and the acidulant react in the presence of water to produce carbon dioxide (i.e., effervescence). As noted earlier, the acidulant should be substantially comprised of one or more non-hydroxy group containing acidulant. Adipic acid, succinic acid, fumaric acid and succinic anhydride are preferred. Succinic anhydride will hydrolyze to form succinic acid.

As the alkaline component of the effervescent couple, sodium bicarbonate, sodium carbonate, potassium carbonate, potassium bicarbonate, calcium carbonate, magnesium carbonate, sodium glycine carbonate and mixtures thereof may be employed.

The amounts of acid and alkaline bicarbonate or carbonate may each separately constitute 25 to 60% (w/w), more preferably 30 to 50% (w/w), of the effervescent composition. The equivalent or stoichiometric ratio of acid to alkaline carbonate or bicarbonate may be within the range of 1:2 to 2:1.

The composition of the present invention can include sweetening agents such as sucrose, aspartame, cyclamic acid salts, acesulfame-K, saccharin acid or its salts, and mixtures thereof. Filler and flow promoting materials can also be employed, for example, silicon dioxide.

To illusethe benefits of the instant invention an effervescent formulation according to Example 1 which follows, was prepared. The amount of ranitidine hydrochloride used in all of the examples is equivalent to 75 mg. ranitidine, i.e., the OTC dose in the United States.) The acidulant was varied, as is shown in Examples 2 through 6 which follow.

EXAMPLE 1

The following prototype powder effervescent histamine $H_2$ antagonist composition was prepared. Although any histamine $H_2$ antagonists could be employed with like results, ranitidine hydrochloride was employed in all examples.

The composition was prepared by blending all ingredients in a twin shell blender until a uniform composition was obtained. The composition had the formula:

| INGREDIENT | %(WT/WT) | AMOUNT(g./sachet) |
| --- | --- | --- |
| Sodium bicarbonate | 45.25 | 2.29 |
| Sodium carbonate (anhydrous) | 4.54 | 0.23 |
| Adipic Acid | 43.86 | 2.22 |
| Sucrose | 2.17 | 0.11 |
| Silicon Dioxide | 0.10 | 0.005 |
| Ranitidine hydrochloride | 1.66 | 0.084 |
| Aspartame | 0.40 | 0.02 |
| Glycine (aminoacetic acid) | 1.98 | 0.10 |
| Sodium Saccharin | 0.04 | 0.002 |
| TOTAL | 100.00 | 5.061 |

EXAMPLE 2

The composition as described in Example 1 was prepared except that instead of 2.22 g/sachet adipic acid, 1.95 g/sachet of citric acid were employed.

EXAMPLE 3

The composition of Example 1 was prepared except that instead of 2.22 g/sachet adipic acid, 2.04 g/sachet of malic acid were employed.

EXAMPLE 4

The composition of Example 1 was prepared except that instead of 2.22 g./sachet adipic acid, 2.29 g/sachet of tartaric acid were employed.

EXAMPLE 5

The composition of Example 1 was prepared except that instead of 2.22 g./sachet adipic acid, 1.80 g/sachet succinic acid were employed.

It should be noted that the amount of acidulant employed in each of Examples 2 through 5 was an amount equivalent to the amount of adipic acid employed in Example 1. In other words, in all of the examples, stoichiometrically equivalent amounts of acidulants were employed.

EXAMPLE 6

Equivalent amounts of each of the compositions of Examples 1, 2, 3, 4 and 5 were stored at ambient temperature and exposed to the atmosphere. The physical appearance of each composition was determined after 12 days of such storage. The results are shown in Table 1 below.

It should be noted that Examples 1 and 5 are examples in accordance with the instant invention, whereas Examples 2, 3 and 4 are examples wherein the acidulant employed is a hydroxy group containing acidulant and as such in not in accordance with the instant invention.

TABLE 1

| EXAMPLE NUMBER | ACIDULANT | PHYSICAL APPEARANCE AFTER 12 DAYS EXPOSURE |
| --- | --- | --- |
| 2 | Citric acid | Heavily caked & not free flowing<br>No discoloration |
| 3 | Malic acid | Heavily caked & not free flowing<br>Strong discoloration |
| 4 | Tartaric acid | Some caking, but free flowing<br>No color change |
| 1 | Adipic acid | No caking and free flowing<br>no color change |
| 5 | Succinic acid | no caking and free flowing<br>no color change |

It should be noted that the compositions of Examples 1 and 5, respectively containing adipic acid and succinic acid, were allowed to remain exposed to the atmosphere for 16 more days. In other words, for a total of four weeks. The compositions of each of Examples 1 and 5 continued to exhibit no caking, were free flowing and showed no color change.

EXAMPLE 7

Equivalent amounts of the compositions according to Examples 2, 3, 1 and 5 were packaged in vials. The vials were closed and stored at 40° C. and thereafter observed. The results are shown in Table 2 below.

TABLE 2

| EXAMPLE NUMBER | ACIDULANT | PHYSICAL APPEARANCE AFTER THE INDICATED PERIOD OF STORAGE |
| --- | --- | --- |
| 2 | Citric acid | Heavily caked & slightly discolored after 3 days |
| 3 | Malic acid | Heavily caked & slightly discolored after 3 days |
| 5 | Succinic acid | Free flowing with very slight color change after 4 weeks, and still free flowing after 10 weeks |

TABLE 2-continued

| EXAMPLE NUMBER | ACIDULANT | PHYSICAL APPEARANCE AFTER THE INDICATED PERIOD OF STORAGE |
|---|---|---|
| 1 | Adipic acid | free flowing with no color change after 4 weeks, and still free flowing with no color change after 13 weeks |

EXAMPLE 8

As noted earlier, the prior art teaches that ranitidine is incompatible with acids. To assess the degree of such incompatibility, the present inventors prepared binary mixtures containing ranitidine plus an acidulant in a 1:1 ratio. These mixtures were then subjected to varied temperature and relative humidity storage conditions, as set forth in Table 3 below.

TABLE 3

| | % Ranitidine Remaining After Storage at: | | |
|---|---|---|---|
| 1:1 mixture of: | 30° C./60% RH | 35° C./75% RH | 40° C./75% RH |
| Ranitidine: Citric acid* | 85.7 | 70.3 | 28.4 |
| Ranitidine: Malic acid** | 63.9 | 18.9 | 2.3 |
| Ranitidine: Tartaric acid* | 97.7 | 67.9 | 37.6 |
| Ranitidine: Adipic acid** | 100.1 | 84.5 | 63.9 |

*Determination made after 8 weeks storage.
**Determination made after 6 weeks storage.

The data of Table 3 was generated utilizing a very high ratio of ranitidine to acid. Additionally, a variation in humidity and temperature was employed. This was done to accelerate any degradation that might occur.

It is abundantly clear from the data of Table 3 that even under the extreme conditions in which ranitidine was evaluated, ranitidine is vastly more stable with adipic acid (a non-hydroxy group containing acidulant) than with citric, malic or tartaric acids (hydroxy group containing acidulants). This is entirely unexpected and surprising.

EXAMPLE 9

To demonstrate that the acidulant employed in the effervescent composition of the present invention should preferably be comprised substantially entirely of non-hydroxy group containing acidulant and more specifically should preferably be devoid of hydroxy group containing acidulants, the following composition was prepared:

| INGREDIENT | Amount (g/sachet) | % (Wt/Wt) |
|---|---|---|
| Sodium Bicarbonate | 2.29 | 43.36 |
| Anhydrous Sodium carbonate | 0.23 | 4.36 |
| Adipic Acid | 2.22 | 42.04 |
| Tartaric Acid | 0.22 | 4.17 |
| Sucrose | 0.11 | 2.08 |
| Silicon Dioxide | 0.005 | 0.09 |
| Ranitidine Hydrochloride | 0.084 | 1.59 |
| Aspartame | 0.02 | 0.38 |
| Glycine | 0.10 | 1.89 |
| Sodium saccharin | 0.002 | 0.04 |
| TOTAL | 5.281 | 100.00 |

The composition of the present example was prepared by admixing the powders as a dry blend, in a twin shell blender, until the mixture was uniform.

Using the same procedure, another composition was made identical to the above composition, however, the tartaric acid was omitted from the composition. Both compositions were stored at 40° C. After six weeks at that temperature the composition containing ranitidine hydrochloride, adipic acid and tartaric acid showed some discoloration. The same composition without the tartaric acid exhibited no discoloration after six week at 40° C. and more importantly, exhibited no discoloration after 13 weeks storage at 40° C. Thus, it is obvious from these results that the acidulant employed in the composition of the present invention should preferably be comprised substantially entirely of non-hydroxy group containing acidulant and most preferably should be devoid of hydroxy group containing acidulant.

Although the instant invention has been described with reference to powders and sachets, it is not limited to that dosage form. Tablets can also be produced. Example 10 which follows illustrates the preparation of tablets in accordance with the present invention.

EXAMPLE 10

The composition is as follows:

| INGREDIENTS | % (Wt/Wt) | Grams/per tablet |
|---|---|---|
| Ranitidine hydrochloride | 1.61 | 0.084 |
| Silicon dioxide | 0.1 | 0.005 |
| Sodium carbonate (anhydrous) | 4.41 | 0.23 |
| Sodium bicarbonate | 43.95 | 2.29 |
| Adipic acid | 42.6 | 2.22 |
| Aspartame | 0.38 | 0.02 |
| Sodium saccharin | 0.04 | 0.002 |
| Glycine | 1.92 | 0.10 |
| Sucrose | 2.11 | 0.11 |
| Sodium benzoate | 2.88 | 0.15 |
| TOTALS | 100.00 | 5.211 |

The above formulation was scaled up for 50 tablets.

Sodium benzoate was included in the formula as a soluble lubricant. One skilled in the art of tablet formation would appreciate that other lubricants could also be utilized.

The ranitidine hydrochloride was screened through a 40 mesh screen. The silicon dioxide was passed through a 20 mesh screen. The remaining ingredients were passed through a 30 mesh screen. The ingredients were dry blended and the resultant mixture was compressed on a F3 Single Punch Press. The tablets so produced were satisfactory in all respects.

It should be appreciated that the examples set forth above are merely illustrative of the present invention and are not intended to be limiting in any respect. One skilled in the art can, using ordinary skill in the art, modify the formulations illustrated above without departing from the spirit and scope of the invention.

What is claimed is:

1. A powder composition comprising an effective amount of a histamine $H_2$ antagonist, an unreacted acidulant, and an unreacted alkaline material which will react with the acidulant in the presence of water to form carbon dioxide, the acidulant being a non-hydroxy group containing acidulant that is solid at ambient conditions.

2. The composition according to claim 1, wherein the composition is free of hydroxy group containing acidulant.

3. The composition according to claim 1, wherein the non-hydroxy group containing acidulant is selected from the group consisting of adipic acid, succinic acid, fumaric acid, succinic anhydride and mixtures thereof.

4. The composition according to claim 3, wherein the non-hydroxy group containing acidulant is adipic acid.

5. The composition according to claim 3, wherein the non-hydroxy group containing acidulant is succinic acid.

6. The composition according to claim 1, wherein the Histamine $H_2$ antagonist is selected from the group consisting of ranitidine, cimetidine, nizatidine, famotidine and pharmaceutically acceptable salts thereof.

7. The composition according to claim 1, wherein the Histamine $H_2$ receptor antagonist is ranitidine or a pharmaceutically acceptable salt thereof.

8. A tablet comprising an effective amount of a histamine $H_2$ antagonist, an unreacted acidulant, an unreacted alkaline material which will react with the acidulant on contact with water to form carbon dioxide, and a lubricant, said acidulant being a non-hydroxy group containing acidulant that is solid at ambient conditions.

9. The tablet according to claim 8, wherein the Histamine $H_2$ receptor antagonist is selected from the group consisting of ranitidine, cimetidine, nizatidine, famotidine and pharmaceutically acceptable salts thereof.

10. The composition according to claim 9, wherein the Histamine $H_2$ receptor antagonist is ranitidine or a pharmaceutically acceptable salt thereof.

11. The tablet according to claim 8, wherein the non-hydroxy group containing acidulant is selected from the group consisting of adipic acid, succinic acid, fumaric acid, succinic anhydride and mixtures thereof.

12. The composition according to claim 11, wherein the non-hydroxy group containing acidulant is adipic acid.

13. The composition according to claim 11, wherein the non-hydroxy group containing acidulant is succinic acid.

14. The composition according to claim 1, wherein the composition is free of hydroxy group containing acidulant.

15. The tablet according to claim 8 wherein the tablet is free of hydroxy group containing acidulant.

* * * * *